United States Patent
Mitusina

(10) Patent No.: US 8,142,464 B2
(45) Date of Patent: Mar. 27, 2012

(54) FLEXIBLE INNER MEMBER HAVING A FLEXIBLE REGION COMPOSED OF LONGITUDINALLY AND ROTATIONALLY OFFSET PARTIAL CIRCUMFERENTIAL CUTS

(76) Inventor: Miroslav Mitusina, Ruskin, FL (US)

( * ) Notice: Subject to any disclaimer, the term of this patent is extended or adjusted under 35 U.S.C. 154(b) by 399 days.

(21) Appl. No.: 12/506,332

(22) Filed: Jul. 21, 2009

(65) Prior Publication Data

US 2011/0022069 A1 Jan. 27, 2011

(51) Int. Cl.
*A61B 17/14* (2006.01)
(52) U.S. Cl. .......................... 606/180; 604/22
(58) Field of Classification Search ............... 606/79, 606/159, 170, 171, 180; 604/22; 623/1.15
See application file for complete search history.

(56) References Cited

U.S. PATENT DOCUMENTS

| | | |
|---|---|---|
| 4,646,738 A | 3/1987 | Trott |
| 5,152,744 A | 10/1992 | Krause et al. |
| 5,286,253 A | 2/1994 | Fucci |
| 5,322,505 A | 6/1994 | Krause et al. |
| 5,437,630 A | 8/1995 | Daniel et al. |
| 5,510,070 A | 4/1996 | Krause et al. |
| 5,529,580 A | 6/1996 | Kusunoki et al. |
| 5,540,708 A | 7/1996 | Lim et al. |
| 5,620,415 A | 4/1997 | Lucey et al. |
| 5,620,447 A | 4/1997 | Smith et al. |
| 6,053,922 A | 4/2000 | Krause et al. |
| 6,533,749 B1 | 3/2003 | Mitusina et al. |
| 6,656,195 B2 * | 12/2003 | Peters et al. ................. 606/159 |
| 7,276,074 B2 | 10/2007 | Adams et al. |
| 7,338,495 B2 | 3/2008 | Adams |
| 2005/0090849 A1 | 4/2005 | Adams |

FOREIGN PATENT DOCUMENTS

DE  3828478 A1  5/1989

* cited by examiner

*Primary Examiner* — Victor Nguyen

(57) ABSTRACT

A flexible inner member for being rotatably disposed in an angled outer tubular member of a rotary tissue cutting instrument has a flexible region composed of a series of partial circumferential cuts formed through the wall of a tubular body of the inner member. Each cut extends along an arc that defines part of the external circumference of the tubular body. The cuts are uniformly longitudinally spaced in succession along the length of the tubular body corresponding to the flexible region. The cuts are parallel to one another and perpendicular to a central longitudinal axis of the tubular body. The cuts are grouped in duplicative patterns that repeat along the length of the flexible region, there being at least two successive cuts in each pattern. The cuts of each pattern are rotationally offset in succession in a rotational direction about the central longitudinal axis of the tubular body.

20 Claims, 4 Drawing Sheets

FLEXIBLE INNER MEMBER HAVING A FLEXIBLE REGION COMPOSED OF LONGITUDINALLY AND ROTATIONALLY OFFSET PARTIAL CIRCUMFERENTIAL CUTS

BACKGROUND OF THE INVENTION

1. Field of the Invention

The present invention pertains generally to flexible inner members rotatably disposed within angled outer tubular members of rotary surgical tissue cutting instruments wherein the inner member has a flexible region to transmit torque while conforming to the angled configuration of the outer tubular member. More particularly, the present invention pertains to flexible inner members of angled rotary tissue cutting instruments wherein the flexible region comprises longitudinally and rotationally offset partial circumferential cuts formed in a tubular body of the inner member.

2. Brief Discussion of the Related Art

Angled rotary tissue cutting instruments have become widely accepted for use in various surgical procedures to cut anatomical tissue at a surgical site within a patient's body. Angled rotary tissue cutting instruments typically comprise an elongate angled outer tubular member and an elongate flexible inner tubular member rotatably disposed within the angled outer tubular member. A cutting element at a distal end of the inner member is exposed from an opening at a distal end of the outer member to cut anatomical tissue at the surgical site when the inner member is rotated within the outer member. The inner member is ordinarily rotated within the outer member via a powered surgical handpiece coupled to proximal ends of the outer and inner members, with the handpiece being maintained externally of the patient's body. The outer tubular member has one or more angled, curved or bent regions along its length to provide an angled configuration that facilitates positioning of the cutting element at the surgical site when the instrument is introduced in the patient's body, and particularly when the instrument is introduced through a narrow or small size, natural or artificially created entry opening in the patient's body. The inner tubular member is provided with one or more flexible regions to reside within the one or more angled, curved or bent regions of the outer member for transmitting torque to rotate the cutting element while conforming to the angled configuration of the outer member. The angled configuration of the outer member is particularly beneficial in facilitating positioning of the cutting element at the surgical site where there is a non-straight path in the body from the entry opening to the surgical site. In such cases, angled rotary tissue cutting instruments are usually better suited to access the surgical site more easily and quickly, and with less trauma to the patient, than are rotary tissue cutting instruments in which the outer tubular member is longitudinally straight. In many surgical procedures performed using rotary tissue cutting instruments, the internal lumen of the inner tubular member is used to transmit suction to the surgical site to aspirate anatomical tissue and/or fluid through the inner member. In addition, an annular gap or clearance between the internal diameter of the outer member and the external diameter of the inner member is commonly used as an irrigation passage to supply irrigation fluid to the surgical site.

One design advantage in rotary tissue cutting instruments is to minimize the external diametric size of the outer member to allow introduction of the instrument in the patient's body through entry openings as small as possible in size and/or to facilitate advancement of the instrument to the surgical site with as little trauma as possible to the patient. Another design advantage in rotary tissue cutting instruments is to maximize the internal diameter of the inner tubular member so that aspiration of tissue and/or fluid through the inner member can be accomplished with greater efficiency and with less risk of clogging. Yet a further design advantage in rotary tissue cutting instruments is to maintain an appropriate annular clearance between the internal diameter of the outer tubular member and the external diameter of the inner member to avoid jamming of the instrument and/or to provide efficient flow of irrigation fluid between the outer and inner members. In angled rotary tissue cutting instruments, it would also be a design advantage to minimize the number of structural components or parts required for the flexible region of the inner member, thereby reducing manufacturing and material costs, as well as reducing the risk of operational problems arising from structural complexity and/or multiple structural components. The foregoing design advantages must necessarily be balanced against the need to maintain sufficient strength and rigidity in the flexible inner members of angled rotary tissue cutting instruments when transmitting torque via the flexible regions, particularly considering that angled rotary tissue cutting instruments must oftentimes be designed to operate at high rotational speeds and to withstand the forces imposed when cutting very hard or tenacious anatomical tissue.

Various designs previously proposed for the flexible regions in the inner members of angled rotary tissue cutting instruments have limited the extent to which the aforementioned design advantages can be optimized in angled rotary tissue cutting instruments. Some of the deficiencies associated with prior designs proposed for the flexible regions in the inner members of angled rotary tissue cutting instruments include increased radial thickness of the annular wall of the inner tubular member along the flexible region resulting in a larger external diameter and/or smaller internal diameter for the inner member, structural complexity and/or the need for multiple assembled structural parts to form the flexible region, constriction of the internal diameter of the flexible region when transmitting torque within an angled region of the outer tubular member, longitudinal stretching of the flexible region, and insufficient strength and rigidity in the flexible region limiting the range of bend angles over which the flexible region is able to effectively transmit torque. Designs for the flexible regions of inner tubular members of angled rotary tissue cutting instruments that result in the inner tubular member being of larger external diametric size normally require that the angled outer tubular member be of larger external diametric size in order to rotatably receive the inner member while maintaining the appropriate annular clearance between the outer and inner members. Designs for the flexible regions of inner tubular members of angled rotary tissue cutting instruments that result in the inner tubular member having a smaller internal diameter or that result in constriction of the internal diameter will typically have a negative impact on the ability to aspirate tissue and/or fluid through the inner tubular member. Designs for the flexible regions of inner tubular members of angled rotary tissue cutting instruments that involve structural complexity and/or multiple assembled structural parts generally result in the inner tubular member being of higher cost and at increased risk of operational problems. Operational problems are also more likely to occur in inner tubular members of angled rotary tissue cutting instruments in which the design for the flexible region in the inner member makes the flexible region prone to longitudinal stretching.

In some flexible inner tubular members of angled rotary tissue cutting instruments, the flexible regions are formed of a plurality of concentric spirals, typically an inner spiral, a middle spiral and an outer spiral attached to one another at their ends. Each spiral is formed by winding a flat strip of material, with alternating spirals being wound in opposite rotational directions about a central longitudinal axis of the inner member as represented by U.S. Pat. No. 4,646,738 to Trott, U.S. Pat. No. 5,286,253 to Fucci and U.S. Pat. No. 5,540,708 to Lim et al. It has also been proposed to provide shafts having flexible regions made up of concentric coils of wound wire of circular cross-section, rather than wound flat strips of material, as represented by U.S. Pat. No. 5,437,630 to Daniel et al and U.S. Pat. No. 5,529,580 to Kusunoki et al and by German Patent DE 3828478 A1. The radial dimension or thickness of the annular wall of a flexible region comprised of multiple concentric spirals or coils tends to be substantial since it includes the individual thickness of each spiral or coil. Flexible regions of this type tend to result in flexible inner tubular members of larger external diametric sizes requiring diametrically larger outer tubular members, and/or of smaller internal diameters leading to reduced aspiration capability. In addition, flexible inner tubular members having these types of flexible regions will ordinarily be associated with higher material costs due to the multiple structural components involved and with higher manufacturing costs associated with producing and assembling the different structural components. The risk of operational problems may be greater due to the presence of multiple structural components and increased structural complexity, and the securement or attachment sites for the multiple spirals or coils present the potential for structural failure.

Another design approach for the flexible regions in the flexible inner tubular members of angled rotary tissue cutting instruments involves a single continuous spiral or helical cut formed in an inner tube, and one or more layers of spiral wrap disposed over the cut region of the inner tube as represented by U.S. Pat. No. 6,533,749 B1 to Mitusina et al and U.S. Pat. No. 6,656,195 B2 to Peters et al, and by United States Patent Application Publication No. US2005/0090849 A1 to Adams. The one or more layers of spiral wrap are each formed by winding a flat strip of material over the cut region in the inner tube and attaching the ends of the strip to the tube. The helical cut and the one or more layers of spiral wrap are arranged so that their rotational direction or turn about a central longitudinal axis of the inner member alternate in opposite directions. The Peters et al patent discloses the helical cut in the inner tube as having a dovetail pattern. The extent to which it is possible to minimize the radial dimension or thickness of the annular wall of a flexible region comprised of an inner tube and one or more layers of spiral wrap over a cut region of the tube is limited by the fact that the wall thickness of the inner tube and the thickness of each layer of spiral wrap contribute cumulatively to the radial dimension of the annular wall formed by the flexible region. Furthermore, the inner tube and each spiral wrap are separate structural components assembled during manufacture, giving rise to issues of increased cost and structural complexity.

U.S. Pat. No. 7,338,495 B2 to Adams is an example of a flexible region in a flexible inner tubular member of an angled rotary surgical cutting instrument formed of a helical cut in an inner tube, a layer of adhesive disposed over the cut region of the inner tube, and a heat shrunk sleeve disposed over the cut region of the inner tube and being bonded thereto by the adhesive. The helical cut is formed in the inner tube in a stepped pattern. Again, the radial thickness of the annular wall formed by the flexible region is made up of the individual thicknesses of the inner tube wall, the adhesive layer, and the wall of the sleeve. The flexible region requires multiple parts or materials in addition to the inner tube, and is still somewhat complicated from a manufacturing standpoint.

Flexible regions have also been provided in the inner tubular members of angled rotary tissue cutting instruments by forming disconnected slots or openings in an inner tube, with the slots being arranged in a slot pattern that repeats along the length of the flexible region as illustrated by U.S. Pat. No. 5,152,744, U.S. Pat. No. 5,322,505 and U.S. Pat. No. 5,510,070 to Krause et al, U.S. Pat. No. 5,620,415 to Lucey et al, and U.S. Pat. No. 5,620,447 to Smith et al. The Krause et al patents present an embodiment in which the slot pattern is made up of two partial circumferential slots disposed at longitudinally offset or spaced positions along the inner tube. The two slots are also rotationally offset 180° from each other about the central longitudinal axis of the inner tube, and the slots are perpendicular to the central longitudinal axis of the inner tube. The slot pattern repeats with every third successive slot and at every third successive longitudinal spaced position along the inner tube. The wall of the tube that extends in a circumferential direction between the ends of each slot forms a tab, and the wall of the tube between longitudinally adjacent slots forms an annular ring. The flexible region resulting from this slot pattern is composed of a series of interconnected U-shaped leaf springs, each U-shaped leaf spring being formed by a pair of longitudinally adjacent rings connected to one another by a tab.

The Krause et al patents present another embodiment in which the slot pattern is similar to the aforementioned slot pattern but is made up of two pairs of opposed partial circumferential slots respectively disposed at longitudinally offset or spaced positions along the inner tube. The first pair of opposed slots are rotationally offset 180° from each other at a first longitudinal position along the inner tube. The second pair of opposed slots are rotationally offset 180° from each other at a second, successive longitudinal spaced position along the inner tube. The second pair of opposed slots are rotationally offset 90° from the first pair of opposed slots. The slots are perpendicular to the central longitudinal axis of the inner tube, and the pairs of opposed slots that comprise the flexible region are uniformly offset or spaced in longitudinal succession along the inner tube. The slot pattern repeats with every third successive pair of opposed slots and at every third successive longitudinal spaced position along the inner tube. The wall of the tube that extends in a circumferential direction between the ends of the slots in each pair of opposed slots forms two opposed tabs. The wall of the tube between longitudinally adjacent pairs of opposed slots forms an annular ring. Each ring within the flexible region is interconnected with a preceding longitudinally adjacent ring by a first pair of opposed tabs and is interconnected with a succeeding longitudinally adjacent ring by a second pair of opposed tabs rotationally offset 90° from the first pair of opposed tabs. The flexible region resulting from this slot pattern is composed of a series of interconnected H-shaped leaf springs. The tabs within the U-shaped and H-shaped leaf springs of Krause et al's flexible regions are of minimal size in the circumferential direction, making the leaf springs prone to breakage when transmitting torque and/or limiting the strength and rigidity of the inner member.

The Krause et al patents further disclose pliable material disposed within the slots, a sheath disposed over the flexible region, and an intermediate tube between the outer and inner tubular members, all of which result in higher costs and/or greater risk of operational problems due to added structural complexity and/or parts, increased external diametric size of the outer tubular member, and/or diminished aspiration efficiency due to decreased internal diametric size of the inner tubular member.

The Smith et al patent pertains to a rotary surgical instrument comprising concentric outer, intermediate and inner tubular members. The intermediate tubular member has a rigid bend region, the outer tubular member has a flexible region disposed over the bend region, and the inner tubular member has a flexible region disposed within the bend region. The flexible regions are like those of the Krause et al patents where the flexible region is made up of a series of interconnected U-shaped leaf springs, and the flexible regions employed by Smith et al thusly share the same disadvantages as the flexible regions of Krause et al. The Lucey et al patent pertains to a "punch" type surgical instrument comprising a rigid outer tubular member having a bend region, an intermediate tubular member having a flexible region disposed within the bend region, and an inner tubular member having a flexible region disposed within the bend region. The flexible regions are like those employed in the instrument of the Smith et al patent and thusly have the same drawbacks. The Smith et al and Lucey et al instruments being comprised of three concentric tubes results in numerous additional disadvantages including increased structural complexity and parts leading to higher costs and greater risk of operational problems, increased external diametric size of the outer tubular member, and/or decreased internal diametric size of the inner tubular member.

U.S. Pat. No. 6,053,922 to Krause et al pertains to a flexible shaft for reaming the medullary space in bones. In contrast to the flexible inner members of angled rotary tissue cutting instruments, the flexible shaft of Krause et al '922 is not shown to be rotatably disposed within a rigid outer tubular member, and is thusly not subject to the same design considerations as the inner members of rotary tissue cutting instruments and of angled rotary tissue cutting instruments in particular. In further distinction to the flexible inner tubular members of angled rotary tissue cutting instruments, the flexible shaft of Krause et al '922 is said to be an elongated tubular member of substantial wall thickness. A flexible inner tubular member of substantial wall thickness would be undesirable in an angled rotary tissue cutting instrument because it would result in a reduction in the internal diametric size of the inner member which would reduce aspiration capability, and/or it would require an outer member of larger external diametric size to accommodate the inner member, which would require larger size entry openings in the patient's body for introduction of the instrument. The tubular member of Krause et al '922 comprises a slot, said to be of substantial width, extending spirally around the tubular member in a pattern that forms pairs of complementary, mating interlocking teeth and recesses in the tubular member that Krause et al '922 relies on to transmit torque. The tooth and recess slot pattern repeats without interruption, such that each complementary, mating interlocking tooth and recess pair borders the next complementary, mating interlocking tooth and recess pair. The slot configuration thusly consists entirely of the configurations of the teeth and recesses of the particular slot pattern, resulting in an "unbound joint".

Despite the numerous different design approaches previously proposed for the flexible inner members of angled rotary tissue cutting instruments, it was not recognized until the present invention to provide a flexible region in an inner member made up of partial circumferential cuts or slots formed in a tubular body of the inner member in uniform longitudinal offset or spaced succession along the length of the flexible region, with groups of successive cuts arranged in duplicate patterns of rotational offset or stagger along the length of the flexible region, where the pattern is composed of more than two successive partial circumferential cuts or slots rotationally offset or staggered in succession by less than 90° in a rotational direction about the central longitudinal axis of the tubular body. Until the present invention, it was not recognized that a flexible region resulting from the aforesaid longitudinal and rotational distribution and arrangement of partial circumferential cuts or slots in a tubular body of an inner member of an angled rotary tissue cutting instrument would provide numerous design advantages, including the advantages of structural simplicity and minimal parts, elimination of the need for the flexible region to include additional structure or material over the cut or slotted region of the tubular body or within the cuts or slots themselves, appropriate rigidity and torsional strength, reduced risk of operational problems, manufacturing simplicity, decreased material and manufacturing costs, resistance to stretching in the longitudinal axial direction of the inner member, preservation of the integrity of the internal diameter of the inner member, and the capability to transmit torque within angled outer tubular members having a broad range of bend angles.

SUMMARY OF THE INVENTION

The present invention is generally characterized in a flexible inner member for being rotatably disposed within an angled outer tubular member of a rotary tissue cutting instrument. The outer tubular member includes a distal end, a longitudinal internal passage, an open proximal end communicating with the passage, an angled region between the distal and proximal ends, and an opening in the distal end communicating with the internal passage. The flexible inner member has a distal end, a proximal end, a tubular body between the distal and proximal ends of the inner member, a cutting element at the distal end of the inner member, and a flexible region for being disposed within the angled region of the outer tubular member. When the inner member is rotatably disposed within the internal passage of the outer tubular member, the cutting element is exposed from the opening in the outer tubular member, and the flexible region is disposed within the angled region to transmit torque to rotate the cutting element while conforming to the configuration of the angled region. The tubular body of the inner member has a central longitudinal axis and a cylindrical wall with a wall thickness between external and internal circumferential surfaces of the cylindrical wall. The external circumferential surface defines an external circumference of the tubular body.

The flexible region is composed of a series of partial circumferential cuts formed in the wall of the tubular body entirely through the wall thickness thereof. The cuts are uniformly or equally longitudinally spaced or offset in succession along the length of the tubular body corresponding to the flexible region. Each cut extends along an arc in a rotational or circumferential direction about the central longitudinal axis from a first or starting end of the cut to a second or terminating end of the cut. The arc defines part of the external circumference of the tubular body. Each cut is bisected by a central plane perpendicular to the central longitudinal axis, and the central planes of the cuts are parallel to one another along the central longitudinal axis. Each cut is associated with a partial circumferential wall segment of the tubular body extending in the rotational or circumferential direction from the second end of the cut to the first end of the cut. The arc of the cut and the arc of the external circumferential surface of the tubular body along the partial circumferential wall segment together define the complete external circumference of the tubular body. Between each pair of longitudinally adjacent cuts, there is a complete circumferential wall segment of the tubular body. Each cut has a width in a direction parallel to the central longitudinal axis, the width of the cuts being uniform or constant along the flexible region. The first and second ends of each cut extend in the longitudinal direction of the tubular body with an outward curvature in opposed directions.

Groups of successive cuts are arranged in duplicate patterns of rotational offset or stagger that repeat along the length of the tubular body corresponding to the flexible region. Each pattern comprises a group of more than two of the cuts in longitudinal succession along the tubular body. Preferably, each pattern comprises a first cut, a second cut, a third cut, and a fourth cut in longitudinal succession along the tubular body. In addition to the cuts of each pattern being uniformly longitudinally offset or spaced in succession along the tubular body, the cuts of each pattern are rotationally or circumferentially offset or staggered in succession in the rotational direction about the central longitudinal axis. The first or starting ends of the first cuts of the patterns are in a starting end first rotational position on the tubular body radial to the central longitudinal axis. The first or starting ends of the second cuts of the patterns are in a starting end second rotational position on the tubular body radial to the central longitudinal axis and rotationally or circumferentially offset in the rotational direction from the starting end first rotational position by a starting end rotational offset. The first or starting ends of the third cuts of the patterns are in a starting end third rotational position on the tubular body radial to the central longitudinal axis and rotationally offset in the rotational direction from the starting end second rotational position by the starting end rotational offset. The first or starting ends of the fourth cuts of the patterns are in a starting end fourth rotational position on the tubular body radial to the central longitudinal axis and rotationally offset in the rotational direction from the starting end third rotational position by the starting end rotational offset. The starting end rotational offset is less than 90°.

Various objects, advantages and benefits of the present invention will become apparent from the following detailed description of the invention taken in conjunction with the accompanying drawings.

DETAILED DESCRIPTION OF THE INVENTION

Figure 1:
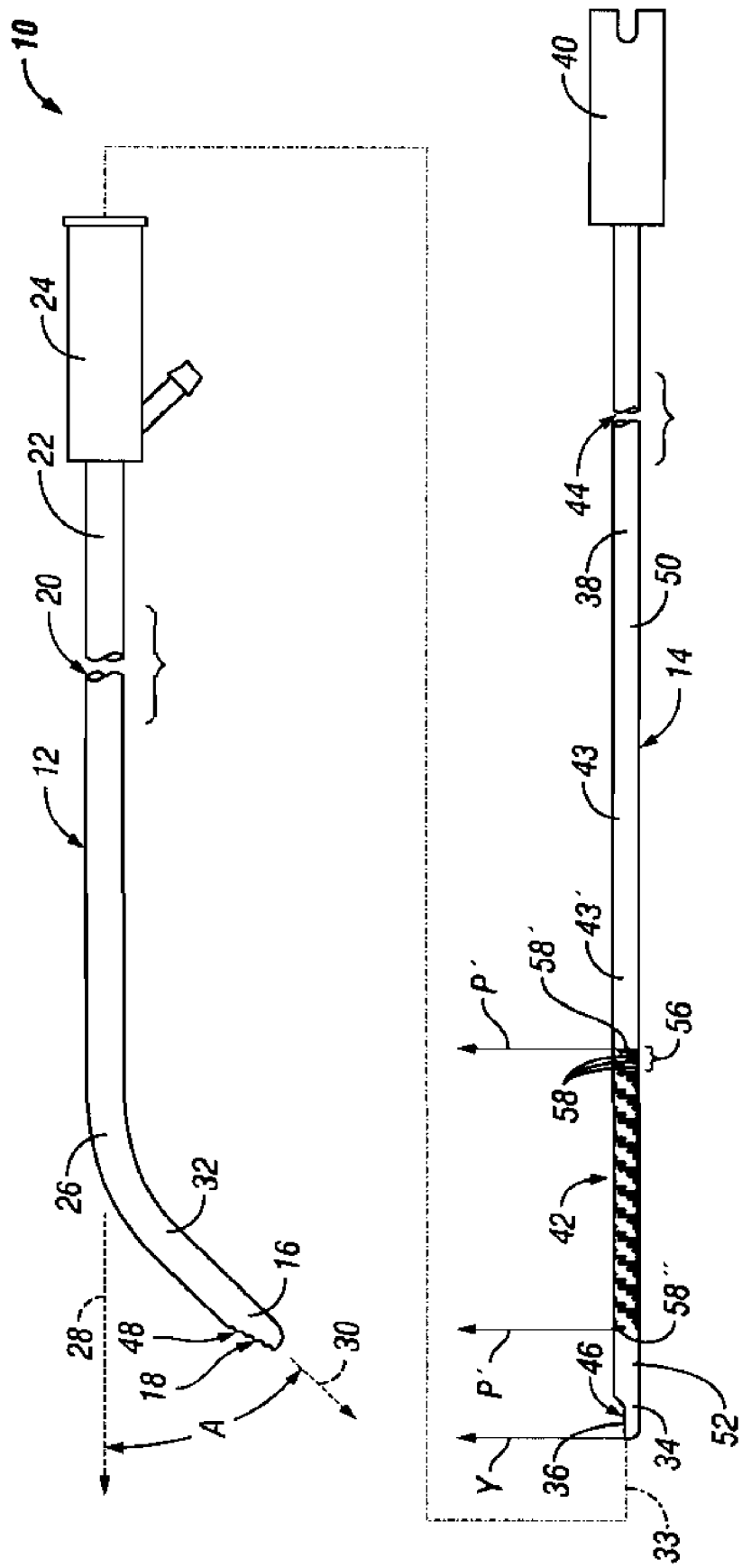
FIG. 1 is an exploded side view of an angled rotary tissue cutting instrument comprising an angled outer tubular member and a flexible inner member for being rotatably received in the outer tubular member.

An angled rotary tissue cutting instrument 10 is depicted in FIG. 1 and comprises an elongate angled outer tubular member 12 and an elongate flexible inner member 14 for being rotatably disposed within the outer tubular member 12. The outer tubular member 12 has a distal end 16 with an opening 18 therein in communication with the internal passage 20 in the outer tubular member. The outer tubular member 12 has a proximal length portion 22 terminating at an open proximal end typically secured in an outer member hub 24 designed for engagement with a powered surgical handpiece (not shown) in a conventional manner. The outer tubular member 12 is provided with one or more angled, curved or bent regions 26 along the length thereof, such that the outer tubular member 12 has an angled configuration. Each angled region 26 in the outer tubular member 12 defines a bend angle A corresponding to the angle defined between length portions of the outer tubular member 12 that are joined by the angled region. The outer tubular member 12, for example, has a bend angle A defined between the central longitudinal axis 28 of the proximal length portion 22 of the outer member 12 and a central longitudinal axis 30 of a distal length portion 32 of the outer member 12 which is joined to the proximal length portion 22 by the angled region 26. The size and the direction of the bend angle A can vary individually for each angled region 26. The outer tubular member 12 illustrated in FIG. 1 has one angled region 26 with a bend angle A extending in a downward direction from proximal length portion 22.

As a result of its angled configuration, the outer tubular member 12 is not longitudinally straight along its length. However, the outer tubular member 12 can initially be provided in a longitudinally straight configuration, without the one or more angled regions 26, and can be bent from the longitudinally straight configuration in any suitable manner to obtain the angled configuration desired for the outer tubular member. Accordingly, bending the outer tubular member 12 from the longitudinally straight configuration to the desired angled configuration will involve bending the outer tubular member 12 as needed to obtain the desired number of angled regions 26 at the desired location or locations along the length of the outer tubular member and extending in the desired direction or directions at the desired bend angle or angles A. It should be appreciated that the outer tubular member 12 can be bent from the longitudinally straight configuration to the angled configuration with or without the flexible inner member 14 disposed within the outer tubular member 12. The outer tubular member 12 is rigid in a longitudinally straight configuration but is able to be bent to form the desired angled region(s) when sufficient bending force is applied. The outer tubular member 12 is or remains rigid after bending to form the one or more angled regions.

The inner member 14 has a central longitudinal axis 33, a distal end 34 provided with or formed as a cutting element 36, a proximal length portion 38 terminating at a proximal end that is typically secured in an inner member hub 40, and one or more flexible regions 42 between the cutting element 36 and the inner member hub 40. The one or more flexible regions 42 impart flexibility to the inner member that allows the inner member to bend along its central longitudinal axis 33. When the inner member 14 is assembled with the outer tubular member 12 to cut anatomical tissue, the inner member 14 will extend through the outer member hub 24 and will be rotatably disposed within the internal passage 20 of the outer tubular member 12 with the cutting element 36 exposed from the opening 18 in the outer member, with the one or more flexible regions 42 disposed within the one or more angled regions 26 of the outer member, and with the inner member hub 40 disposed proximally of the outer member hub 24 for engagement with the powered surgical handpiece. The powered surgical handpiece is operated in a conventional manner to rotate the inner member 14 relative to and within the outer tubular member 12, and the one or more flexible regions 42 transmit torque to rotate the cutting element 36 while conforming to the angled configuration of the outer tubular member 12. As the inner member 14 is rotated within the outer tubular member 12, the cutting element 36 exposed from the opening 18 will cut anatomical tissue contacted with the cutting element 36.

The inner member 14 comprises a cylindrical tubular body 43 coaxial with the central longitudinal axis 33 and having an internal lumen 44 extending longitudinally within the tubular body. The tubular body 43 preferably has an open end forming the proximal end of the inner member 14 and preferably extends from the proximal end of the inner member 14 to the cutting element 36, as is the case for tubular body 43. Preferably, the tubular body 43 is an integral and unitary or monolithic tube from the proximal end of the inner member 14 to the cutting element 36, as is the case for tubular body 43. Accordingly, the flexible inner member 14 is a flexible inner tubular member. As described further below, the one or more flexible regions 42 are each formed by a repeating pattern 56 of partial circumferential cuts or slots 58 formed through the wall of the tubular body 43, where each pattern 56 is composed of more than two, and preferably four, partial circumferential cuts or slots 58 longitudinally offset or spaced in succession along the tubular body 43 and rotationally offset or staggered in succession about the central longitudinal axis 33 of the tubular body.

The cutting element 36 can have various cutting configurations effective to cut anatomical tissue including the various cutting configurations conventionally used for the inner members of rotary tissue cutting instruments. The cutting configuration for the cutting element 36 can be designed for side cutting and/or end cutting. The cutting element 36 can be a structure that is hollow or provided with an interior cavity or channel in communication with the lumen 44 of the tubular body 43. The cutting element 36 can be a structure formed separate from and attached to the tubular body 43. The distal end 34 of the inner tubular member 14 can have an opening 46 therein in communication with the internal lumen 44 of the inner member 14, and the opening 46 can communicate with the lumen 44 via the interior cavity or channel in the structure that forms the cutting element 36. The cutting configuration for the cutting element 36 can include one or more cutting surfaces or edges along the periphery of the opening 46 as is the case for the cutting element 36 of the inner member 14 depicted in FIG. 1. The cutting surfaces or edges of the cutting element 36 can be defined by cutting tooth formations, as is also the case for the cutting element 36 of inner member 14. The cutting surfaces or edges of the cutting element 36 can be defined by flute formations as in a bur tip, for example.

The distal end 16 of the outer tubular member 12 can be provided with or formed as a cutting element 48 that cooperates with the cutting element 36 of the inner member 14 to cut anatomical tissue. The cutting element 48 can have various cutting configurations effective to cut anatomical tissue in cooperation with the cutting element 36, and the various cutting configurations conventionally used for the outer members in rotary tissue cutting instruments can be used for the cutting configuration of the cutting element 48. The cutting configuration for the cutting element 48 can include one or more cutting surfaces or edges along the periphery of the opening 18 as is the case for the cutting element 48 of the outer tubular member 12 depicted in FIG. 1. The cutting surfaces or edges of the cutting element 48 can be defined by cutting tooth formations, as is also the case for the cutting element 48. Typically, the cutting elements 36 and 48 cooperate to cut anatomical tissue as a result of rotation of the one or more cutting surfaces or edges of the cutting element 36 past the one or more cutting surfaces or edges of the cutting element 48. Depending on the cutting configuration of the inner member cutting element 36, it should be appreciated that the outer tubular member 12 can be without a cutting element such that tissue cutting is performed entirely by the inner member. Furthermore, the opening 18 in the outer member can be a side opening or an end opening depending on the cutting configuration of the inner member cutting element 36.

As the cutting element 36 is rotated, the opening 46 in the inner member 14 will come into alignment with the opening 18 in the outer tubular member 12, allowing anatomical tissue and/or fluid to enter the lumen 44 of the inner member 14 through the aligned openings 18 and 46. Through the application of vacuum or suction to the lumen 44, typically via a connection at a proximal end of the instrument 10 in a conventional manner, the lumen 44 can serve as an aspiration passage by which suction is applied at the surgical site via the aligned openings 18 and 46 and by which fluid and/or anatomical tissue is/are drawn into the lumen 44 through the aligned openings 18 and 46 for evacuation through the instrument 10.

In order for the inner member 14 to rotate within the outer tubular member 12 without jamming, an appropriate annular clearance or gap is present between the internal diameter of the outer tubular member 12 and the external diameter of the inner member 14 when the members 12 and 14 are assembled to cut tissue. The annular clearance or gap between the outer and inner members 12 and 14 can serve as an irrigation passage by which irrigation fluid supplied to the annular clearance, typically from a proximal end of the instrument 10, is conveyed distally and released at the surgical site through the opening 18 in the outer tubular member 12.

The inner member 14 can have a single flexible region 42 of sufficient length and at the appropriate location to reside in and conform to the configuration of one or more angled regions 26 in the outer tubular member 12. The inner member 14 can have a plurality of flexible regions 42, each of sufficient length and at the appropriate location to reside in and conform to the configuration of a corresponding angled region 26 in the outer tubular member 12. Each flexible region 42 can be disposed adjacent and/or between rigid or non-flexible length segments of the tubular body 43. The inner member 14 is an example of one having a single flexible region 42 disposed between rigid or non-flexible length segments 50 and 52 of the tubular body 43, the single flexible region 42 being located appropriately along the length of the inner member 14 to reside within the single angled region 26 in the outer tubular member 12 and being of sufficient length to conform to the configuration of the single angled region 26 when the inner member 14 is assembled with the outer member 12 to cut anatomical tissue. The length segment 50 of the tubular body 43 is part of the proximal length portion 38, which will be disposed within the proximal length portion 22 of the outer member 12 when the inner member is assembled with the outer member to cut anatomical tissue. The length segment 50 may thusly be considered a proximal length segment. The length segment 52 of the tubular body 43 may be considered a distal length portion or segment and will be disposed within the distal length portion 32 of the outer member 12 when the inner and outer members are assembled to cut anatomical tissue.

Figure 2:
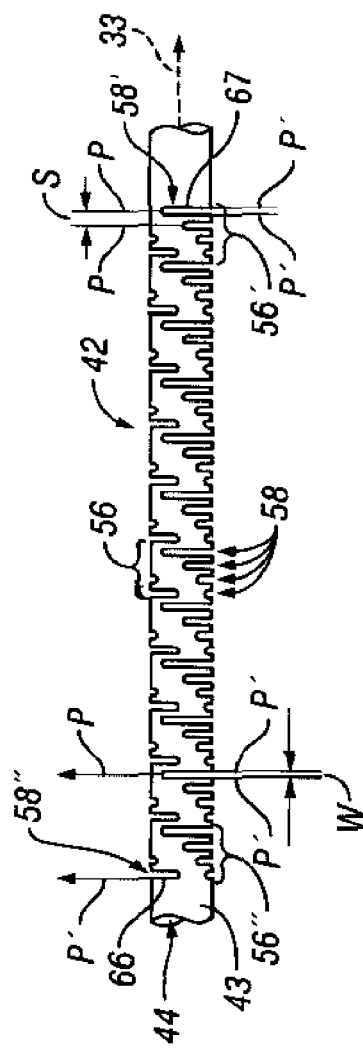
FIG. 2 is an enlarged broken side view of the flexible inner member of the angled rotary tissue cutting instrument depicting a flexible region of the flexible inner member.
Figure 3:
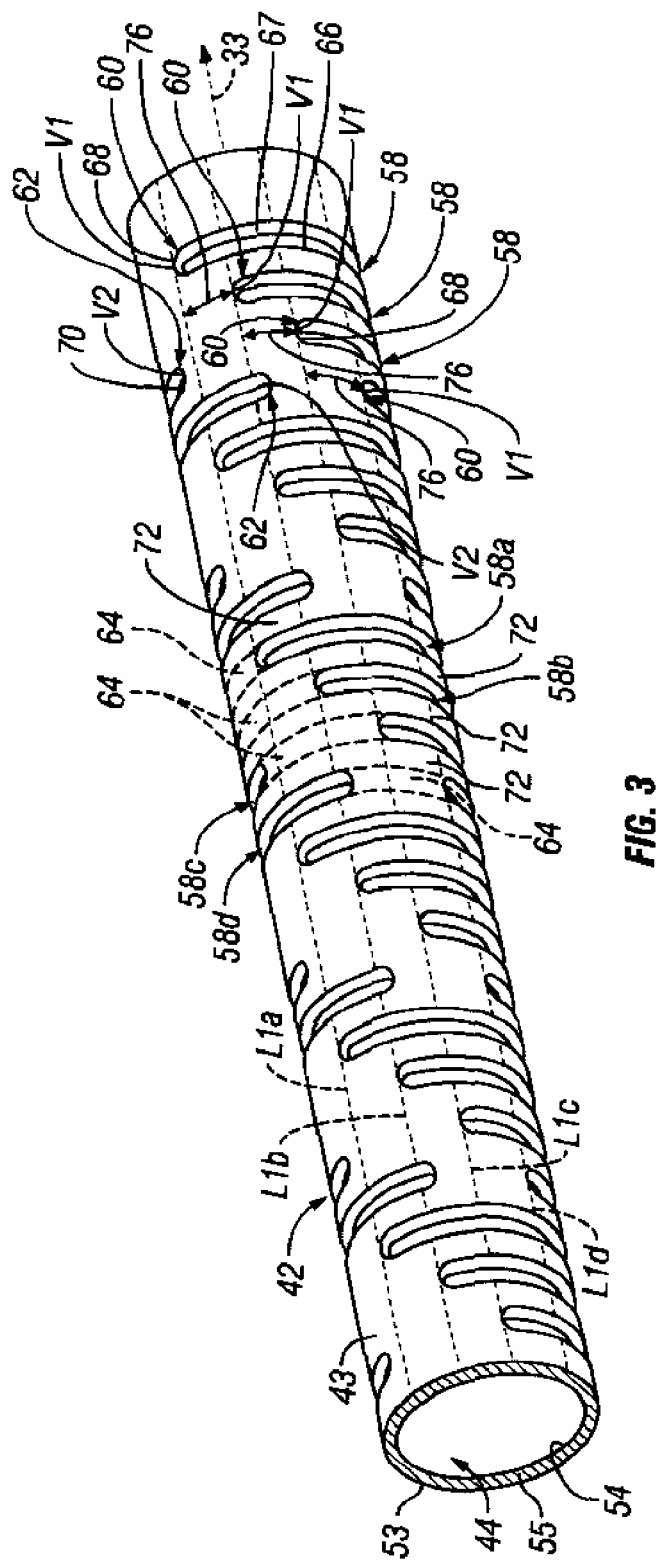
FIG. 3 is an enlarged broken perspective view of a tubular body of the flexible inner member having a series of partial circumferential cuts formed therein in longitudinally offset or spaced succession along the length of the tubular body, and wherein groups of successive cuts are arranged in duplicate patterns of rotational offset that repeat along the length of the tubular body corresponding to the flexible region of FIG. 2.
Figure 4:
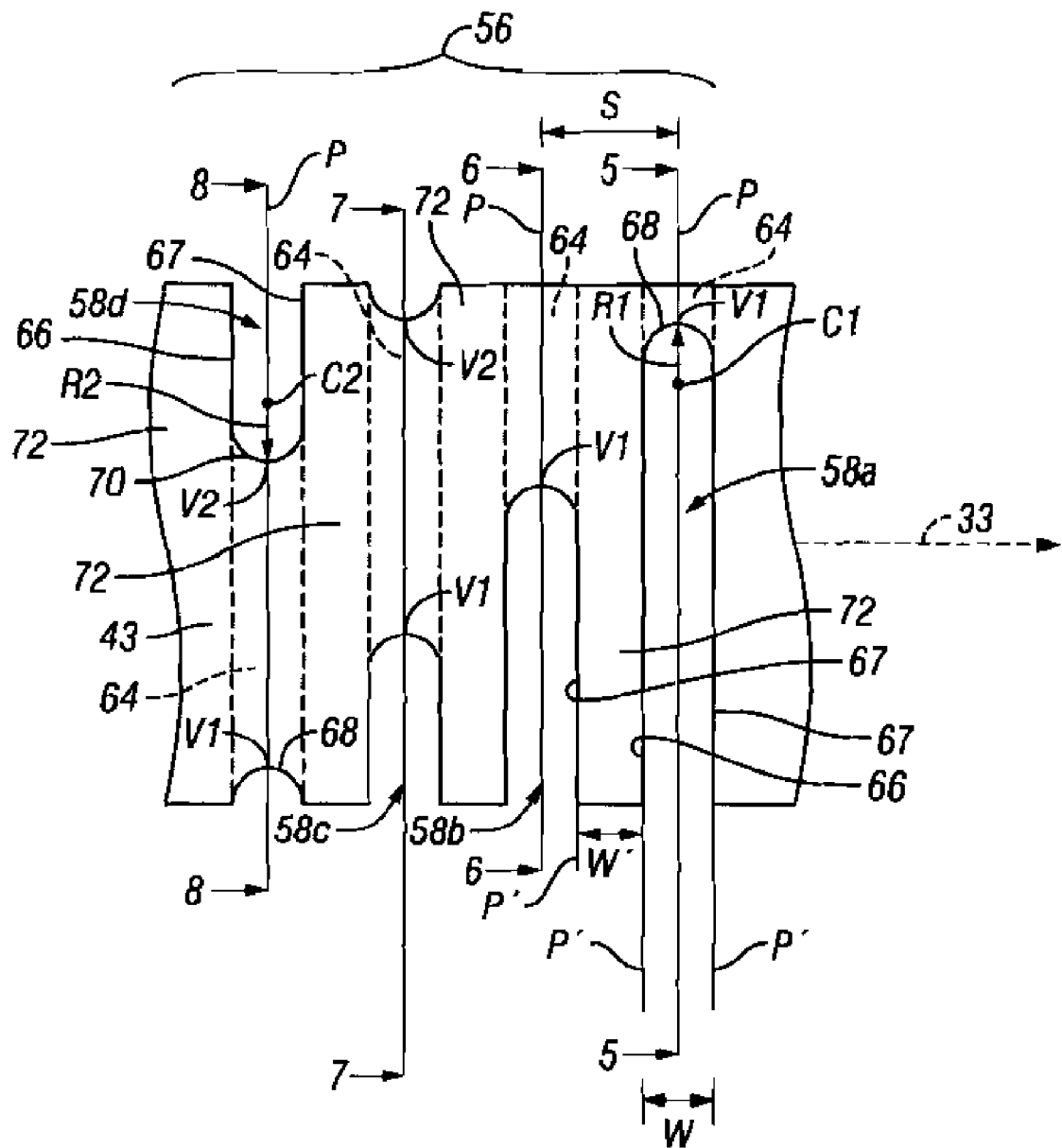
FIG. 4 is a broken, detailed side view of the tubular body depicting the arrangement of partial circumferential cuts in the pattern of rotational offset.

The flexible region 42, which is best depicted in FIGS. 2 and 3, comprises a series of partial circumferential cuts or slots 58 formed in the tubular body 43 of the inner member 14 in uniform longitudinal offset or spaced succession and with groups of successive cuts 58 arranged in duplicative patterns 56 of rotational offset or stagger that repeat along the length of the tubular body 43 corresponding to the length of the flexible region 42. The tubular body 43 has a cylindrical annular wall with an external circumferential surface 53, an internal circumferential surface 54 defining the lumen 44, and a radial wall thickness 55 between the external and internal circumferential surfaces. The external and internal circumferential surfaces 53 and 54 respectively define the external and internal diameters of the inner member 14. The wall of the tubular body 43 in cross-section perpendicular to the central longitudinal axis 33 has an external circumference defined by the circumference of the external circumferential surface 53. Prior to the cuts or slots 58 being formed therein, the wall of the tubular body 43 along the flexible region 42 and along the length segments 50 and 52 is a rigid, integral and unitary, one piece or monolithic, solid, annular wall coaxial with the central longitudinal axis 33. Each cut or slot 58 extends entirely through the wall thickness 55 of the cylindrical annular wall of the tubular body 43 from the external circumferential surface 53 to the internal circumferential surface 54 in a direction radial and perpendicular to the central longitudinal axis 33, as explained further below. Each cut 58 is a partial circumferential cut. That is, each cut 58 extends in an arc in a rotational or circumferential direction about the central longitudinal axis 33 that is less than the entire or complete external circumference of the wall of the tubular body 43, i.e. less than 360° about the central longitudinal axis 33. Each cut 58 extends in the rotational or circumferential direction about the central longitudinal axis 33 from a starting or first end 60 of the cut to a terminating or second end 62 of the cut, with there being a solid partial circumferential wall segment 64 of the tubular body 43 extending in the rotational or circumferential direction from the terminating end 62 to the starting end 60 of the cut. The partial circumferential wall segment 64 extends in an arc in the rotational or circumferential direction about the central longitudinal axis 33 that is equal to 360° minus the arc of the associated cut 58. As explained further below, the arc of the partial circumferential cut 58 is defined by the arc of the radius of the external circumferential surface 53 from one end of the cut 58 to the other. The arc of the partial circumferential wall segment 64 is defined by the arc of the external circumferential surface 53 from one end of the cut 58 to the other. Together the arc of the partial circumferential cut 58 and the arc of the partial circumferential wall segment 64 associated with the cut 58 form or define the complete external circumference of the wall of the tubular body 43 and a complete 360° rotation or revolution about the central longitudinal axis 33. Each cut 58 is bisected lengthwise, i.e. along its arc, in the circumferential direction by a central plane P perpendicular to the central longitudinal axis 33 and cross-sectional to the tubular body 43 as best seen in FIGS. 2 and 4, it being noted that the cuts 58 are respectively identified in FIG. 4 as 58a, 58b, 58c and 58d. The central planes P of the cuts 58 are parallel to one another and are uniformly or equally longitudinally offset or spaced in succession along the central longitudinal axis 33, i.e. along the length of the tubular body 43 corresponding to the length of the flexible region 42.

As best seen with reference to FIGS. 3 and 4, each cut 58 is bounded or circumscribed by a peripheral surface or wall formed by the wall thickness 55 of the tubular body 43 between the external and internal circumferential surfaces 53 and 54. The peripheral surface has a peripheral edge along the external circumferential surface 53 comprising a pair of parallel side peripheral edge segments 66 and 67, an arcuate starting end or first end peripheral edge segment 68 connecting the side peripheral edge segments 66 and 67 at starting end 60, and an arcuate terminating end or second end peripheral edge segment 70 connecting the side peripheral edge segments 66 and 67 at terminating end 62. The side peripheral edge segments 66 and 67 extend in the rotational or circumferential direction and are disposed respectively in planes P' parallel to the central plane P of the cut 58. The side peripheral edge segments 66 and 67 extend along the external circumference of the tubular body 43 in their respective planes P'. Each cut 58 has a width W between the planes P' of its side peripheral edge segments 66 and 67 in a direction perpendicular to the planes P', the width W being parallel to the central longitudinal axis 33 and being centrally divided by the central plane P of the cut. The arcuate starting end peripheral edge segment 68 and the arcuate terminating end peripheral edge segment 70 of each cut 58 have an outward or convex curvature extending transversely between the side peripheral edge segments 66 and 67 of the cut. The starting end and terminating end peripheral edge segments 68 and 70 extend across the width W of the cut 58 between the side peripheral edge segments 66 and 67 in the longitudinal direction of the tubular body 43. The starting end peripheral edge segment 68 of each cut 58 has a radius of curvature R1 extending from a center of curvature C1 disposed in the central plane P of the cut in alignment with the apex or vertex V1 of the curve defining the arcuate starting end peripheral edge segment 68 of the cut. The terminating end peripheral edge segment 70 of each cut 58 is like the starting end peripheral edge segment 68 but is curved outward in a direction opposite the outward curvature of its starting end peripheral edge segment 68. The terminating end peripheral edge segment 70 of each cut 58 has its radius of curvature R2 extending from a center of curvature C2 disposed in the central plane P of the cut in alignment with the apex or vertex V2 of the curve defining the arcuate terminating end peripheral edge segment 70 of the cut. The tubular body 43 has a cross-section in plane P of the cut wherein, looking proximally, the radius of curvature R1 extends outward from the center of curvature C1 to the vertex V1 toward the counterclockwise direction and the radius of curvature R2 extends outward from the center of curvature C2 to the vertex V2 toward the clockwise direction. As a result of the opposed outward curvatures of the starting end and terminating end peripheral edge segments 68 and 70, the starting and terminating ends 60 and 62 of the cut 58 have a convex curvature.

As best shown with reference to FIGS. 4-8 for the cuts 58 that are respectively designated as cuts 58a, 58b, 58c and 58d, each cut 58 has an arc L in the central plane P of the cut 58 extending in the circumferential direction from the vertex V1 of the starting end peripheral edge segment 68 to the vertex V2 of the terminating end peripheral edge segment 70 of the cut. Looking proximally, i.e. toward the proximal end of the inner member 14 as depicted in FIGS. 5-8, the arc L of each cut 58 extends clockwise about the central longitudinal axis 33 from the vertex V1 to the vertex V2, and the rotational or circumferential direction is therefore clockwise about the central longitudinal axis 33. The arc L of each cut 58 is the arc formed or defined by the radius of the external circumferential surface 53 in the rotational direction from vertex V1 to the vertex V2 of the cut, looking proximally, in the plane P of the cut. The arc L of each cut 58 thusly corresponds to a part or portion of the complete external circumference of the wall of the tubular body 43. The partial circumferential wall segment 64 associated with each cut 58 has an arc along the external circumferential surface 53 in the central plane P of the cut 58. Looking proximally in FIGS. 5-8, the arc of each partial circumferential wall segment 64 extends in the rotational or circumferential direction, i.e. clockwise in the case of flexible region 42, about the central longitudinal axis 33 along the external circumferential surface 53 from the vertex V2 of the terminating end peripheral edge segment 70 of the cut 58 to the vertex V1 of the starting end peripheral edge segment 68 of the cut 58. The arc of the partial circumferential wall segment 64 is the arc formed or defined by the radius of the external circumferential surface 53 in the rotational direction from the vertex V2 to the vertex V1 of the cut, looking proximally, in the plane P of the cut. The arc of each partial circumferential wall segment 64 thusly corresponds to the portion of the complete external circumference along which the wall of the tubular body 43 is solid and not occupied by the associated cut 58.

It should be appreciated that the terms "starting" and "first" used to describe the ends 60 of the cuts 58, the terms "terminating" and "second" used to describe the ends 62 of the cuts 58, and the "clockwise" direction of rotation for the cuts 58 and the wall segments 64 about the central longitudinal axis 33 looking proximally are used herein for explanatory purposes, and not as structural limitations, to assist in understanding the configuration of the cuts 58 and the pattern or arrangement of the cuts 58 on the tubular body 43. Accordingly, the ends 60 could alternatively be considered the terminating or second ends of the cuts 58 and the ends 62 could alternatively be considered the starting or first ends of the cuts. Furthermore, the cuts 58 and wall segments 64 could alternatively be considered as extending in a counterclockwise rotational or circumferential direction about the central longitudinal axis 33 looking proximally, and/or in either a clockwise or counterclockwise rotational or circumferential direction looking distally.

As best seen in FIG. 2, the flexible region 42 extends distally or forwardly along the length of the tubular body 43 from a cut 58 that may be considered a proximalmost or rearward most cut 58' to a cut 58 that may be considered a distalmost or forwardmost cut 58". Each cut 58 has its side peripheral edge segment 66 located distal or forward of its side peripheral edge segment 67. Accordingly, the side peripheral edge segments 66 of the cuts 58 may be considered distal or forward side peripheral edge segments, and the side peripheral edge segments 67 may be considered proximal or rearward side peripheral edge segments. The plane P' of the side peripheral edge segment 66 of the distalmost cut 58" is proximally spaced in parallel from a plane Y at which the distal end 34 of the inner member 14 terminates as depicted in FIG. 1. The plane P' of the side peripheral edge segment 67 of the proximalmost cut 58' is proximally spaced in parallel from the plane Y as depicted in FIG. 1. The flexible region 42 has a length in the longitudinal direction along the tubular body 43 from the plane P' of the distal side peripheral edge segment 66 of the distalmost cut 58" to the plane P' of the proximal side peripheral edge segment 67 of the proximalmost cut 58', the length of the flexible region being parallel to the central longitudinal axis 33.

The cuts 58 of the flexible region 42 are arranged in series or succession along the length of the tubular body 43 in uniform longitudinal offset or spaced relation, with the cuts 58 being arranged along the length of the tubular body 43 that corresponds to the length of the flexible region 42. Except for the proximalmost cut 58', each cut 58 is longitudinally spaced or offset in the distal or forward direction from a longitudinally adjacent or next preceding cut 58. The center to center longitudinal spacing or offset S between longitudinally adjacent cuts 58, i.e. between a cut 58 and a next preceding or next proximal cut 58 and/or between a cut 58 and a next succeeding or next distal cut 58, is the longitudinal distance between and perpendicular to the central planes P of the longitudinally adjacent cuts. The longitudinal spacing or offset S between longitudinally adjacent cuts 58 is uniform, constant or equal throughout the flexible region 42. Between each pair of longitudinally adjacent cuts 58, there is a complete or continuous circumferential wall segment 72 of the tubular body 43 which is connected to the partial circumferential wall segments 64 that are associated with the longitudinally adjacent cuts 58 as best seen in FIGS. 3 and 4. As shown in FIG. 4 for longitudinally adjacent cuts 58a and 58b, each complete circumferential wall segment 72 between longitudinally adjacent cuts 58 has a width W' in the longitudinal direction of the tubular body 43 between and perpendicular to the plane P' of the distal side peripheral edge segment 66 of the proximally situated one of the longitudinally adjacent cuts 58 and the plane P' of the proximal side peripheral edge segment 67 of the next succeeding or distally situated one of the longitudinally adjacent cuts 58. The width W' of the complete circumferential wall segments 72 is uniform, constant or equal throughout the flexible region 42.

Groups of longitudinally successive cuts 58 are arranged in duplicate patterns 56 of rotational offset or stagger along the length of the tubular body 43 corresponding to the length of the flexible region 42. Hence, the flexible region 42 comprises a plurality of repetitions of the pattern 56 along the length of the tubular body 43. Each pattern 56 includes more than two cuts 58 longitudinally offset or spaced in succession along the tubular body 43 and, most preferably, each pattern 56 is made up of four cuts 58 longitudinally offset or spaced in succession along the tubular body 43 as is illustrated for flexible region 42. The four cuts 58 that comprise the pattern 56 are identified in FIGS. 3-8 as cuts 58a, 58b, 58c and 58d. The pattern 56 that contains the proximalmost cut 58' may be considered a first or proximalmost pattern 56', and the pattern 56 that contains the distalmost cut 58" may be considered a last or distalmost pattern 56" of the flexible region 42 as shown in FIG. 2. The patterns 56 between the proximalmost and distalmost patterns 56' and 56" may be considered intermediate patterns.

With reference to FIGS. 4-8, the cut 58a may be considered a first or proximal cut of the pattern 56, the next succeeding or next successive longitudinally adjacent cut 58b that is longitudinally offset or spaced from the first cut 58a in the distal direction may be considered a second cut of the pattern, the next succeeding or next successive longitudinally adjacent cut 58c that is longitudinally offset or spaced from the second cut 58b in the distal direction may be considered a third cut of the pattern, and the next succeeding or next successive longitudinally adjacent cut 58d that is longitudinally offset or spaced from the third cut 58c in the distal direction may be considered a last, fourth or distal cut of the pattern. In the proximalmost pattern 56', the proximalmost cut 58' is the first cut of the pattern. In the distalmost pattern 56", the distalmost cut 58" is the last, fourth or distal cut of the pattern.

The cuts 58a, 58b, 58c and 58d within each complete pattern 56 have their central planes P uniformly or equally longitudinally offset or spaced in succession in the distal direction by the center to center spacing S as described above. With the exception of the proximalmost pattern 56', the first or proximal cut 58a in each pattern has its central plane P longitudinally offset or spaced in succession in the distal direction from the central plane P of the last, fourth or distal cut 58d of the next preceding pattern by the center to center spacing S. Each plane P corresponds to a longitudinal position along the tubular body 43 at which a single partial circumferential cut 58 is formed or provided in the tubular body 43. Each pattern 56 comprises more than two, and preferably four, longitudinal positions along the tubular body 43 at which a single partial circumferential cut 58 is formed or provided in the tubular body 43.

Figure 5:
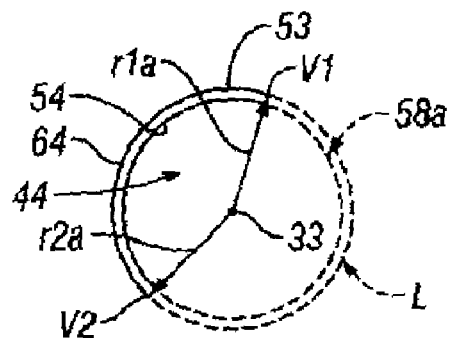
FIG. 5 is a cross-sectional view of the tubular body taken along line 5-5 through a first partial circumferential cut of the pattern in FIG. 4.

In addition to the cuts 58a, 58b, 58c and 58d of each pattern 56 being uniformly longitudinally offset or spaced in succession along the length of the tubular body 43, the cuts 58a, 58b, 58c and 58d of each pattern 56 are rotationally offset or staggered in succession about the central longitudinal axis 33 as seen with reference to FIGS. 4-8. The starting end of the first cut 58a of the pattern 56' may be considered as being in a starting end first rotational position or orientation on the tubular body 43 corresponding to the radial position r1a about the central longitudinal axis 33 of the vertex V1 of the first cut 58a in the central plane P of the first cut 58a as shown in FIG. 5. Looking proximally, FIG. 5 depicts the vertex V1 of the first cut 58a in the central plane P of the first cut 58a at a radial position r1a on the tubular body 43 that is in the upper right quadrant of the tubular body 43. It should be appreciated, however, that the radial position of the vertex V1 for the first cut 58a, and therefore the starting end first rotational position or orientation, can vary 360° about the central longitudinal axis 33 depending on the rotational orientation of the tubular body 43. It should therefore be appreciated that the radial position depicted in FIG. 5 for the vertex V1 for the first cut 58a is provided for purposes of illustration and to establish a reference point for the starting end first rotational position or orientation of the first cut on the tubular body 43, and is not intended as a structural limitation. The arc L of the first cut 58a extends clockwise about the central longitudinal axis 33, looking proximally, from the vertex V1 at the starting end first rotational position 68 to the vertex V2 at the terminating end peripheral edge segment of the first cut 58a as described previously above. The terminating end of the first cut 58a is in a terminating end first rotational position on the tubular body 43 corresponding to the radial position r2a about the central longitudinal axis 33 of the vertex V2 of the first cut 58a in the central plane P of the first cut 58a as shown in FIG. 5.

Figure 6:
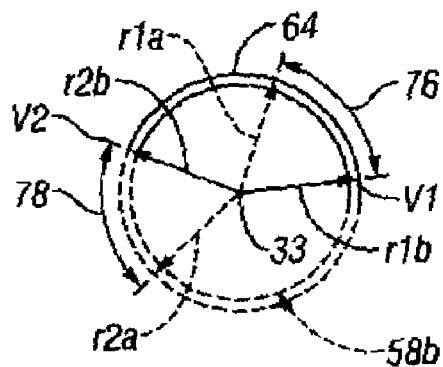
FIG. 6 is a cross-sectional view of the tubular body taken along line 6-6 through a second partial circumferential cut of the pattern in FIG. 4.

The second cut 58b of the pattern 56 is rotationally offset or staggered about the central longitudinal axis 33 relative to the first cut 58a as best seen with reference to FIGS. 4-6. The starting end of the second cut 58b of the pattern 56 may be considered as being in a starting end second rotational position or orientation on the tubular body 43 corresponding to the radial position r1b about the central longitudinal axis 33 of the vertex V1 of the second cut 58b in the central plane P of the second cut 58b as seen in FIG. 6. The vertex V1 of the second cut 58b in the central plane P of the second cut 58b is rotationally or circumferentially offset in the rotational or circumferential direction about the central longitudinal axis 33 from the vertex V1 and starting end first rotational position r1a of the first cut 58a. Looking proximally, the vertex V1 and starting end second rotational position r1b of the second cut 58b are rotationally offset or staggered from the vertex V1 and the starting end first rotational position r1a of the first cut 58a in the clockwise rotational or circumferential direction about the central longitudinal axis 33 by a starting end rotational or circumferential offset 76 that is less than 90°. In a preferred but not limiting embodiment, the starting end rotational offset or stagger 76 is or is about 30°. The arc L of the second cut 58b in the pattern 56 extends clockwise, looking proximally, about the central longitudinal axis 33 from the vertex V1 at the starting end second rotational position r1b to the vertex V2 at the terminating end peripheral edge segment of the second cut 58b as described above. The arc L of the second cut 58b in the pattern 56 extends rotationally or circumferentially in the clockwise direction about the central longitudinal axis 33 beyond the vertex V2 at the terminating end peripheral edge segment of the first cut 58a in the pattern 56. The terminating end of the second cut 58b is in a terminating end second rotational position on the tubular body 43 corresponding to the radial position r2b about the central longitudinal axis 33 of the vertex V2 of the second cut 58b in the central plane P of the second cut. Accordingly, the vertex V2 and the terminating end second rotational position r2b for the second cut 58b in the pattern 56 are rotationally or circumferentially offset or staggered relative to the vertex V2 and the terminating end first rotational position r2a for the first cut 58a in the clockwise direction about the central longitudinal axis 33, looking proximally, by a terminating end rotational or circumferential offset 78. The terminating end rotational or circumferential offset 78 between the vertices V2 of the first and second cuts 58a and 58b in the pattern 56 is less than 90° and preferably is equal to the starting end rotational offset 76.

Figure 7:
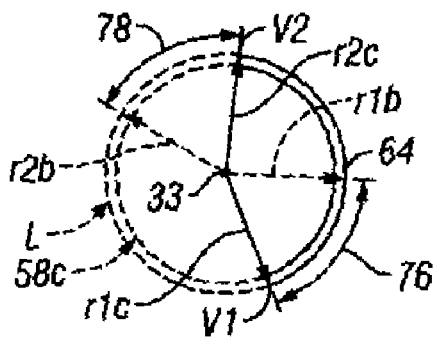
FIG. 7 is a cross-sectional view of the tubular body taken along line 7-7 through a third partial circumferential cut of the pattern in FIG. 4.

The third cut 58c of the pattern 56 is rotationally offset or staggered about the central longitudinal axis 33 relative to the second cut 58b of the pattern 56 as best seen with reference to FIGS. 4, 6 and 7. The starting end of the third cut 58c of the pattern 56 is rotationally or circumferentially offset from the starting end of the second cut 58b of the pattern 56 by the same starting end rotational offset 76 and in the same rotational direction as the starting end rotational offset 76 of the second cut 58b of the pattern 56 from the first cut 58a of the pattern 56. The starting end of the third cut 58c of the pattern 56 may be considered as being in a starting end third rotational position or orientation on the tubular body 43 corresponding to the radial position r1c about the central longitudinal axis 33 of the vertex V1 of the third cut 58c in the central plane P of the third cut 58c as seen in FIG. 7. The vertex V1 of the third cut 58c in the central plane P of the third cut 58c is rotationally or circumferentially offset or staggered in the rotational or circumferential direction about the central longitudinal axis 33 from the vertex V1 and starting end second rotational position r1b of the second cut 58b of the pattern 56. Looking proximally, the vertex V1 and starting end third rotational position r1c of the third cut 58c are rotationally offset from the vertex V1 and the starting end second rotational position r1b of the second cut 58b in the clockwise rotational or circumferential direction about the central longitudinal axis 33 by the starting end rotational or circumferential offset 76. The starting end rotational offset 76 between the vertices V1 of the second and third cuts 58b and 58c is therefore the same amount and in the same rotational direction as the starting end rotational offset between the vertices V1 of the first and second cuts 58a and 58b. The arc L of the third cut 58c in the pattern 56 extends clockwise, looking proximally, about the central longitudinal axis 33 from the vertex V1 at the starting end third rotational position r1c to the vertex V2 at the terminating end peripheral edge segment of the third cut 58c. The arc L of the third cut 58c in the pattern 56 extends rotationally or circumferentially in the clockwise direction about the central longitudinal axis 33 beyond the vertex V2 at the terminating end peripheral edge segment of the second cut 58b in the pattern 56. The terminating end of the third cut 58c is in a terminating end third rotational position on the tubular body 43 corresponding to the radial position r2c about the central longitudinal axis 33 of the vertex V2 of the third cut 58c in the central plane P of the third cut. The vertex V2 and the terminating end third rotational position r2c for the third cut 58c in the pattern 56 are thusly rotationally or circumferentially offset or staggered relative to the vertex V2 and the terminating end second rotational position r2b of the second cut 58b in the clockwise direction about the central longitudinal axis 33, looking proximally, by the terminating end rotational offset 78. The terminating end rotational offset 78 between the vertices V2 of the second and third cuts 58b and 58c in the pattern 56 is the same amount and in the same rotational direction as the terminating end rotational offset 78 between the vertices V2 of the first and second cuts 58a and 58b of the pattern 56.

Figure 8:
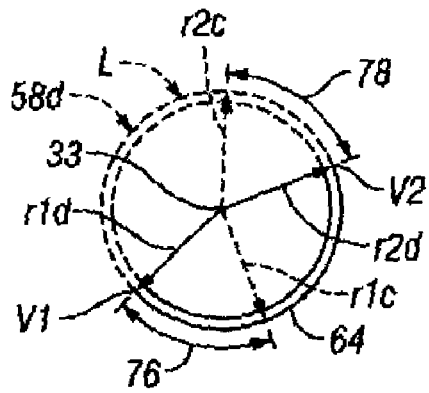
FIG. 8 is a cross-sectional view of the tubular body taken along line 8-8 through a fourth partial circumferential cut of the pattern in FIG. 4.

The fourth cut 58d of the pattern 56 is rotationally offset or staggered about the central longitudinal axis 33 relative to the third cut 58c of the pattern 56 as best seen with reference to FIGS. 4, 7 and 8. The starting end of the fourth cut 58d of the pattern 56 is rotationally or circumferentially offset from the starting end of the third cut 58c of the pattern 56 by the same starting end rotational offset 76 and in the same rotational direction as the starting end rotational offset 76 of the third cut 58c of the pattern 56 from the second cut 58b of the pattern 56. The starting end of the fourth cut 58d of the pattern 56 may be considered as being in a starting end fourth rotational position or orientation on the tubular body 43 corresponding to the radial position r1d about the central longitudinal axis 33 of the vertex V1 of the fourth cut 58d in the central plane P of the fourth cut. The vertex V1 of the fourth cut 58d in the central plane P of the fourth cut 58d is rotationally or circumferentially offset or staggered in the rotational or circumferential direction about the central longitudinal axis 33 from the starting end third rotational radial position r1c of the vertex V1 of the third cut 58c of the pattern 56. The vertex V1 and starting end fourth rotational position r1d of the fourth cut 58d are rotationally offset from the vertex V1 and starting end third rotational position r1c of the third cut 58c in the clockwise direction about the central longitudinal axis 33, looking proximally, by the starting end rotational offset 76. The starting end rotational offset 76 between the vertices V1 of the third and fourth cuts 58c and 58d is the same amount and in the same rotational direction as the starting end rotational offset 76 between the vertices V1 of the second and third cuts 58b and 58c. The arc L of the fourth cut 58d in the pattern 56 extends rotationally or circumferentially in the clockwise direction about the central longitudinal axis 33 beyond the vertex V2 at the terminating end peripheral edge segment of the third cut 58c in the pattern 56. The terminating end of the fourth cut 58d is in a terminating end fourth rotational position on the tubular body 43 corresponding to the radial position r2d about the central longitudinal axis 33 of the vertex V2 of the fourth cut 58d in the central plane P of the fourth cut. The vertex V2 and the terminating end fourth rotational position r2d of the fourth cut 58d in the pattern 56 are rotationally or circumferentially offset or staggered relative to the vertex V2 and the terminating end third rotational position r2c of the third cut 58c in the clockwise direction about the central longitudinal axis 33, looking proximally, by the terminating end rotational offset 78. The terminating end rotational offset 78 between the vertices V2 of the third and fourth cuts 58c and 58d in the pattern 56 is the same amount and in the same rotational direction as the terminating end rotational offset 78 between the vertices V2 of the second and third cuts 58b and 58c of the pattern 56.

The pattern 56 repeats in duplicate along the length of the tubular body 43 that corresponds to the length of the flexible region 42. The cuts 58 of each pattern 56 are uniformly longitudinally offset or spaced in succession on the tubular body 43 and have the same starting end rotational positions or orientations on the tubular body 43 as the corresponding cuts 58 of every other pattern 56 in the flexible region 42. Accordingly, the vertices V1 and the starting end first rotational positions r1a of the first cuts of the patterns 56 are aligned in the longitudinal direction along a starting end first rotational position line L1a parallel with the central longitudinal axis 33; the vertices V1 and the starting end second rotational positions r1b of the second cuts of the patterns 56 are aligned in the longitudinal direction along a starting end second rotational position line L1b parallel with the starting end first rotational position line L1a; the vertices V1 and the starting end third rotational positions of the third cuts of the patterns 56 are aligned in the longitudinal direction along a starting end third rotational position line L1c parallel with the starting end second rotational position line L1b; and the vertices V1 and the starting end fourth rotational positions of the fourth cuts of the patterns 56 are aligned in the longitudinal direction along a starting end fourth rotational position line L1d parallel with the starting end third rotational position line L1c. The starting end second rotational position line L1b is rotationally offset from the starting end first rotational position line L1a in the rotational direction, i.e. clockwise looking proximally, about the central longitudinal axis 33 by the starting end rotational offset 76; the starting end third rotational position line L1c is rotationally offset from the starting end second rotational position line L1b in the rotational direction about the central longitudinal axis 33 by the starting end rotational offset 76; and the starting end fourth rotational position line L1d is rotationally offset from the starting end third rotational position line L1c in the rotational direction about the central longitudinal axis 33 by the starting end rotational offset 76. The pattern 56 repeats with every fifth cut 58 from proximal to distal along the flexible region 42 in the longitudinal direction. The number of pattern repetitions within the flexible region 42 can vary depending on the length of the flexible region and the degree of flexibility desired for the flexible region.

The cuts 58 of each pattern also have the same terminating end rotational positions or orientations on the tubular body 43 as the corresponding cuts 58 of every other pattern 56 in the flexible region 42. The vertices V2 and the terminating end first rotational positions r2a of the first cuts of the patterns 56 are aligned in the longitudinal direction along a terminating end first rotational position line (not shown) parallel with the central longitudinal axis 33; the vertices V2 and the terminating end second rotational positions r2b of the second cuts of the patterns 56 are aligned in the longitudinal direction along a terminating end second rotational position line (not shown) parallel with the terminating end first rotational position line; the vertices V2 and the terminating end third rotational positions r2c of the third cuts in the patterns 56 are aligned in the longitudinal direction along a terminating end third rotational position line (not shown) parallel with the terminating end second rotational position line; and the vertices V2 and the terminating end fourth rotational positions r2d of the fourth cuts in the patterns 56 are aligned in the longitudinal direction along a terminating end fourth rotational position line (not shown) parallel with the terminating end third rotational position line. The terminating end second rotational position line is rotationally offset from the terminating end first rotational position line in the rotational direction, i.e. clockwise looking proximally, about the central longitudinal axis 33 by the terminating end rotational offset 78; the terminating end third rotational position line is rotationally offset from the terminating end second rotational position line in the rotational direction about the central longitudinal axis 33 by the terminating end rotational offset 78; and the terminating end fourth rotational position line is rotationally offset from the terminating end third rotational position line in the rotational direction about the central longitudinal axis 33 by the terminating end rotational offset 78.

In one preferred but not limiting embodiment, the radii of curvature R1 and R2 for the starting end and terminating end peripheral edge segments 68 and 70 of the cuts 58 is or is about one half the width W of the cuts and/or one tenth the center to center longitudinal offset or spacing S between longitudinally adjacent cuts 58; the width W of the cuts is or is about two times the radii of curvature R1 and R2 and/or one fifth the spacing S; the center to center longitudinal offset or spacing S between longitudinally adjacent cuts 58 is or is about five times the width W of the cuts and/or ten times the radii of curvature R1 and R2; and/or the width W' of the complete circumferential wall segments 72 is or is about four times the width W of the cuts and/or eight times the radii of curvature R1 and R2. Moreover, in the preferred but not limiting embodiment, the length of the flexible region 42 is or is about 1.5 inches, the location of the plane P' of the distal side peripheral edge segment 66a of the distalmost cut 58" from the plane Y at which the distal end 34 of the inner member 14 terminates is or is about 0.5 inch, and/or the location of the plane P' of the proximal side peripheral edge segment 66b of the proximalmost cut 58' from the plane Y is or is about 2.0 inches. The arc L of the cuts 58 is or is about 250°, and the arc of the partial circumferential wall segments 64 is or is about 110°. The starting end rotational offset 76 is or is about 30°; The rotational offset between the starting ends of the first and third cuts is or is about 60°; the rotational offset between the starting ends of the second and fourth cuts is or is about 60°; and/or the rotational offset between the starting ends of the first and fourth cuts is or is about 90°. The three starting end rotational offsets within each pattern add up to a total rotational offset between the starting ends of the first and fourth cuts of or about 90°. The terminating end rotational offset 78 is or is about 30°; the rotational offset between the terminating ends of the first and third cuts is or is about 60°; the rotational offset between the terminating ends of the second and fourth cuts is or is about 60°; and/or the rotational offset between the terminating ends of the first and fourth cuts is or is about 90°. The three terminating end rotational offsets within each pattern add up to a total rotational offset between the terminating ends of the first and fourth cuts of or about 90°. In the preferred but not limiting embodiment, there are twelve repetitions of the pattern 56 along the flexible region 42. In a particularly preferred but not limiting embodiment, the cuts 58 have a radii of curvature R1 and R2 of 0.004 inch, a width W of 0.008 inch and a center to center longitudinal offset or spacing S of 0.04 inch, and the complete circumferential wall segments 72 have a width W' of 0.032 inch. In an alternative particularly preferred but not limiting embodiment, the cuts 58 have a radii of curvature R1 and R2 of 0.002 inch, a width W of 0.004 inch and a center to center longitudinal offset or spacing S of 0.02 inch, and the complete circumferential wall segments 72 have a width W' of 0.16 inch.

The flexible region 42 has numerous advantages including, but not limited to, appropriate rigidity and torsional strength, the ability to transmit torque at bend angles of up to 90°, greater resistance to stretching in the longitudinal direction of the inner member 14, and preservation of the integrity of the internal diameter of the tubular body 43 when transmitting torque during rotation of the inner member 14 within the angled outer tubular member 12. The flexible region 42 has the further advantage of not requiring any additional structural component(s) and/or material(s) over or within the cuts 58 in order to operate effectively as the flexible region for an inner member of an angled rotary tissue cutting instrument. An additional advantage is that the annular wall thickness of the inner member 14 along the flexible region 42 can be better minimized in order to better minimize the external diameter of the inner member and/or to better maximize the internal diameter of the inner member. Also, eliminating the need for additional structural components and/or materials presents the advantage of allowing the flexible region 42 to be produced at lower cost and with greater structural simplicity for a reduced risk of operational problems. Although the flexible region 42 does not require any additional structural component(s) over the cuts 58, it is possible to provide a very thin-walled sleeve or sheath over the cut region of the tubular body while retaining the aforementioned advantages. The flexible region 42 is especially well-suited for use with an angled outer tubular member 12 having a bend angle A of up to 90°.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An angled rotary tissue cutting instrument for cutting anatomical tissue, comprising
an elongate angled outer tubular member having a distal end, a longitudinal internal passage, an open proximal end communicating with said passage, an angled region between said distal end and said proximal end, and an opening in said distal end communicating with said passage; and
a flexible inner member for being rotatably disposed within said outer tubular member, said inner member having a distal end, a proximal end, a tubular body between said distal end of said inner member and said proximal end of said inner member, a cutting element at said distal end of said inner member, said cutting element being exposed from said opening to cut anatomical tissue when said inner member is rotatably disposed within said outer tubular member, and a flexible region for being disposed within said angled region to transmit torque to rotate said cutting element while conforming to the configuration of said angled region when said inner member is rotated within said outer tubular member, said tubular body having a central longitudinal axis and a cylindrical wall with an external circumferential surface, an internal circumferential surface, a wall thickness between said external circumferential surface and said internal circumferential surface, and an external circumference defined by said external circumferential surface, said flexible region comprising a series of disconnected partial circumferential cuts formed in said wall of said tubular body entirely through said wall thickness, each of said cuts extending along an arc in a rotational direction about said central longitudinal axis from a first end of said cut to a second end of said cut, said arc of each of said cuts forming part of said external circumference of said tubular body and being disposed in a plane perpendicular to said central longitudinal axis of said tubular body, said planes of said cuts being parallel to one another in uniform spaced relation along the length of said flexible region, said cuts being arranged on said tubular body in repeating patterns of rotational offset along the length of said flexible region, each of said patterns comprising a first cut, a second cut in adjacent longitudinal succession from said first cut, and at least a third cut in adjacent longitudinal succession from said second cut, said first ends of said second cuts being rotationally offset from said first ends of said first cuts in said rotational direction about said central longitudinal axis by a rotational offset, and said first ends of said third cuts being rotationally offset from said first ends of said second cuts in said rotational direction about said central longitudinal axis by said rotational offset.

2. The angled rotary tissue cutting instrument recited in claim 1 wherein said rotational offset is less than 90°.

3. The angled rotary tissue cutting instrument recited in claim 2 wherein said rotational offset is 30°.

4. The angled rotary tissue cutting instrument recited in claim 2 wherein each of said patterns further comprises a fourth cut in adjacent longitudinal succession from said third cut, said first ends of said fourth cuts being rotationally offset from said first ends of said third cuts in said rotational direction but said central longitudinal axis by said rotational offset.

5. The angled rotary tissue cutting instrument recited in claim 4 wherein said rotational offset is 30°.

6. The angled rotary tissue cutting instrument recited in claim 4 wherein each of said cuts is associated with a solid partial circumferential wall segment of said tubular body extending in said rotational direction about said central longitudinal axis from said second end of said cut to said first end of said cut.

7. The angled rotary tissue cutting instrument recited in claim 6 wherein said flexible region includes solid complete circumferential wall segments of said tubular body respectively disposed between longitudinally adjacent ones of said cuts and connected to said partial circumferential wall segments of said longitudinally adjacent ones of said cuts.

8. An angled rotary tissue cutting instrument for cutting anatomical tissue, comprising an elongate angled outer tubular member having a distal end, a longitudinal internal passage, an open proximal end communicating with said passage, an angled region between said distal end and said proximal end, and an opening in said distal end communicating with said passage; and a flexible inner member for being rotatably disposed within said outer tubular member, said inner member having a distal end, a proximal end, a tubular body between said distal end of said inner member and said proximal end of said inner member, a cutting element at said distal end of said inner member, said cutting element being exposed from said opening to cut anatomical tissue when said inner member is rotatably disposed within said outer tubular member, and a flexible region for being disposed within said angled region to transmit torque to rotate said cutting element while conforming to the configuration of said angled region when said inner member is rotated within said outer tubular member, said tubular body having a central longitudinal axis and a cylindrical wall with an external circumferential surface, an internal circumferential surface, a wall thickness between said external circumferential surface and said internal circumferential surface, and an external circumference defined by said external circumferential surface, said flexible region comprising a series of partial circumferential cuts formed in said wall of said tubular body entirely through said wall thickness, each of said cuts being circumscribed by a peripheral edge comprising parallel side peripheral edge segments extending in a circumferential direction about said central longitudinal axis, a first end peripheral edge segment connecting said side peripheral edge segments at a first end of said cut, and a second end peripheral edge segment connecting said side peripheral edge segments at a second end of said cut, said first end peripheral edge segment extending transversely between said side peripheral edge segments with an outward curvature defined by a radius of curvature, said second end peripheral edge segment extending transversely between said side peripheral edge segments with an outward curvature defined by said radius of curvature in a direction opposite said curvature of said first end peripheral edge segment, each of said cuts being bisected by a plane centered between said side peripheral edge segments and perpendicular to said central longitudinal axis, said planes of said cuts being parallel and uniformly spaced along the length of said flexible region, each of said cuts having a width between said side peripheral edge segments perpendicular to said plane of said cut and parallel to said central longitudinal axis, said cuts being arranged on said tubular body in repeating patterns of rotational offset along the length of said flexible region, each of said patterns comprising a first cut, a second cut, a third cut and a fourth cut in longitudinal succession along said tubular body and uniformly rotationally offset in succession in a rotational direction about said central longitudinal axis by a rotational offset between said first end of said second cut and said first end of said first cut in said rotational direction, by said rotational offset between said first end of said third cut and said first end of said second cut in said rotational direction, and of said rotational offset between said first end of said fourth cut and said first end of said third cut in said rotational direction.

9. The angled rotary tissue cutting instrument recited in claim 8 wherein said radius of curvature is one half said width of said cuts.

10. The angled rotary tissue cutting instrument recited in claim 8 wherein said first cut, said second cut, said third cut, and said fourth cut are longitudinally offset in succession along said tubular body by a longitudinal offset corresponding to the uniform spacing between said planes of said cuts, and said radius of curvature is one tenth said longitudinal offset.

11. The rotary tissue cutting instrument recited in claim 10 wherein said width is one fifth said longitudinal offset.

12. The angled rotary tissue cutting instrument recited in claim 8 wherein said radius of curvature is 0.004 inch, said width is 0.008 inch and the uniform spacing between said planes of said cuts is 0.04 inch.

13. The angled rotary tissue cutting instrument recited in claim 8 wherein said radius of curvature is 0.002 inch, said width is 0.004 inch and the uniform spacing between said planes of said cuts is 0.02 inch.

14. The angled rotary tissue cutting instrument recited in claim 8 wherein said rotational offset is 30°.

15. An angled rotary tissue cutting instrument for cutting anatomical tissue, comprising an elongate angled outer tubular member having a distal end, a longitudinal internal passage, an open proximal end communicating with said passage, an angled region between said distal end and said proximal end, and an opening in said distal end communicating with said passage; and a flexible inner member for being rotatably disposed within said outer tubular member, said inner member having a distal end, a proximal end, a tubular body between said distal end of said inner member and said proximal end of said inner member, a cutting element at said distal end of said inner member, said cutting element being exposed from said opening to cut anatomical tissue when said inner member is rotatably disposed within said outer tubular member, and a flexible region for being disposed within said angled region to transmit torque to rotate said cutting element while conforming to the configuration of said angled region when said inner member is rotated within said outer tubular member, said tubular body having a central longitudinal axis and a cylindrical wall with an external circumferential surface, an internal circumferential surface, a wall thickness between said external circumferential surface and said internal circumferential surface, and an external circumference defined by said external circumferential surface, said flexible region comprising a series of partial circumferential cuts formed in said wall of said tubular body entirely through said wall thickness, each of said cuts being circumscribed by a peripheral edge comprising parallel side peripheral edge segments extending in a circumferential direction about said central longitudinal axis, an arcuate starting end peripheral edge segment connecting said side peripheral edge segments at a starting end of said cut, and an arcuate terminating end peripheral edge segment connecting said side peripheral edge segments at a terminating end of said cut, said starting end peripheral edge segment and said terminating end peripheral edge segment each having a curvature with a vertex disposed in a central plane of said cut between said side peripheral edge segments and perpendicular to said central longitudinal axis, each of said cuts extending along an arc in a rotational direction about said central longitudinal axis from said vertex of said starting end peripheral edge segment to said vertex of said terminating end peripheral edge segment, said arc defining part of said external circumference, said central lanes of said cuts being parallel to one another and being uniformly spaced along said central longitudinal axis, said cuts being arranged in a plurality of duplicative patterns along the length of said flexible region, each of said patterns including a first cut, a second cut, a third cut and a fourth cut in longitudinal succession along said tubular body, said vertices of said starting end peripheral edge, segments of said first cuts of said patterns being at a starting end first rotational position on said tubular body radial to said central longitudinal axis, said vertices of said starting end peripheral edge segments of said second outs of said patterns being at a starting end second rotational position on said tubular body radial to said central longitudinal axis and offset in a rotational direction about said axis from said starting end first rotational position by a starting end rotational offset, said vertices of said starting end peripheral edge segments of said third cuts of said patterns being at a starting end third rotational position on said tubular body radial to said central longitudinal axis and offset in said rotational direction about said axis from said starting end second rotational position by said starting end rotational offset, said vertices of said starting end peripheral edge segments of said fourth cuts of said patterns being at a starting end fourth rotational position on said tubular body radial to said central longitudinal axis and offset in said rotational direction about said axis from said starting end rotational third position by said starting end rotational offset.

16. The angled rotary tissue cutting instrument recited in claim 15 wherein said starting end rotational offset is less than 90°.

17. The angled rotary tissue cutting instrument recited in claim 16 wherein said starting end rotational offset is 30°.

18. The angled rotary tissue cutting instrument cited in claim 15 wherein said arc of each of said cuts has a length of 250°.

19. The angled rotary tissue cutting instrument recited in claim 15 wherein said vertices of said terminating end peripheral edge segments of said first cuts of said patterns are at a terminating end first rotational position on said tubular body radial to said central longitudinal axis, said vertices of said terminating end peripheral edge segments of said second cuts of said patterns are at a terminating end second rotational position on said tubular body radial to said central longitudinal axis and offset in said rotational direction about said axis from said terminating end first rotational position by a terminating end rotational offset, said vertices of said terminating end peripheral edge segments of said third cuts of said patterns are at a terminating end third rotational position on said tubular body radial to said central longitudinal axis and offset in said rotational direction about said axis from said terminating end second rotational position by said terminating end rotational offset, said vertices of said terminating end peripheral edge segments of said fourth cuts of said patterns are at a terminating end fourth rotational position on said tubular body radial to said central longitudinal axis and offset in said rotational direction about said axis from said terminating end third rotational position by said terminating end rotational offset.

20. The angled rotary tissue cutting instrument recited in claim 19 wherein said terminating end rotational offset is equal to said starting end rotational offset.

* * * * *